United States Patent [19]

Friese

[11] 4,359,357

[45] Nov. 16, 1982

[54] METHOD OF MAKING TAMPON WITH A NON-WOVEN WRAP

[75] Inventor: Axel Friese, Wuppertal, Fed. Rep. of Germany

[73] Assignee: Dr. Carl Hahn, G.m.b.H, Dusseldorf, Fed. Rep. of Germany

[21] Appl. No.: 255,149

[22] Filed: Apr. 17, 1981

Related U.S. Application Data

[62] Division of Ser. No. 99,771, Dec. 3, 1979, Pat. No. 4,294,253.

[30] Foreign Application Priority Data

Dec. 20, 1978 [DE] Fed. Rep. of Germany ....... 2855179

[51] Int. Cl.³ ....................... B32B 31/10; B32B 31/18
[52] U.S. Cl. .................................... 156/201; 128/285; 128/290 P; 128/296; 156/204; 156/217; 156/227; 156/251
[58] Field of Search ............... 156/200, 204, 213, 217, 156/227, 251, 201; 128/285, 290 P, 296

[56] References Cited

U.S. PATENT DOCUMENTS

| | | | |
|---|---|---|---|
| 3,746,592 | 7/1973 | Nystrand et al. | 156/227 |
| 3,868,287 | 2/1975 | Lewyckyj | 156/227 |
| 3,968,798 | 7/1976 | Hokanson | 128/290 P |

Primary Examiner—Caleb Weston
Attorney, Agent, or Firm—Jason Lipow

[57] ABSTRACT

A catamenial tampon is provided in the form of absorbent material enveloped by a liquid permeable cover which is then folded and compressed into a cylindrical shape. The enveloped absorbent material is in the form of a flat cushion and is first folded into front, central and rear sections with the front and rear sections overlying the central section. A withdrawal cord is looped around the first folded cushion which is then folded around the withdrawal cord and compressed into the final tampon shape. The resulting tampon expands when wet into a cup-shaped configuration.

5 Claims, 11 Drawing Figures

U.S. Patent  Nov. 16, 1982  Sheet 1 of 2  4,359,357
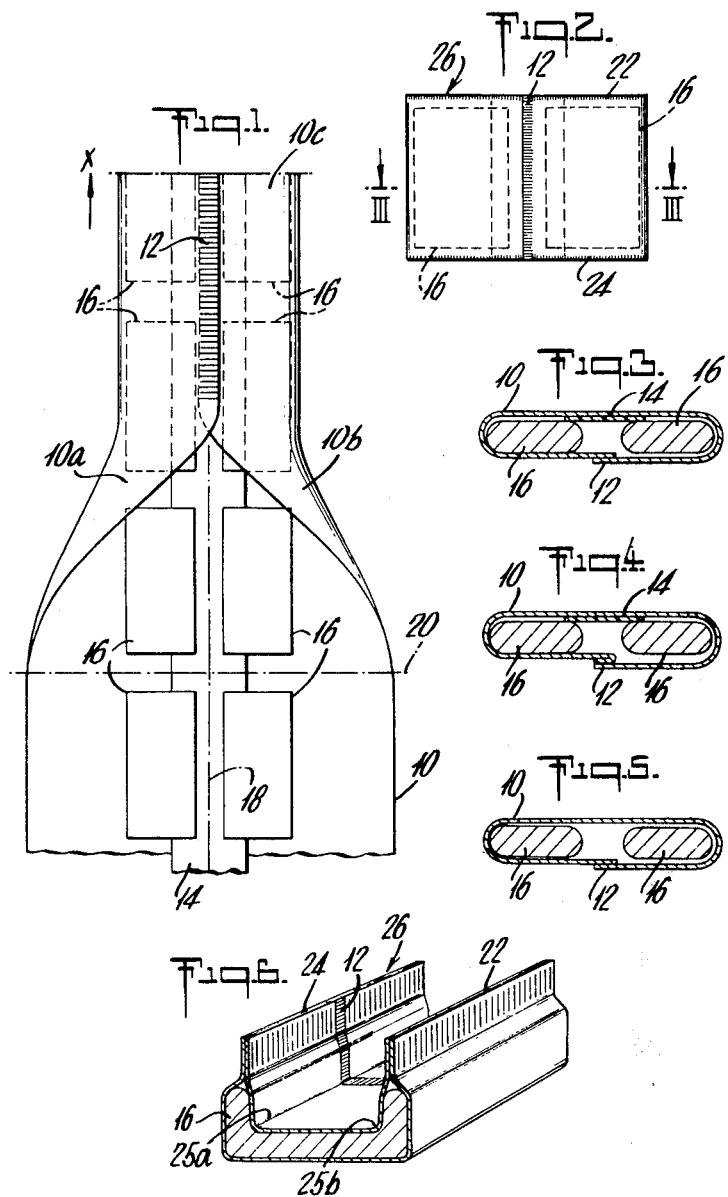

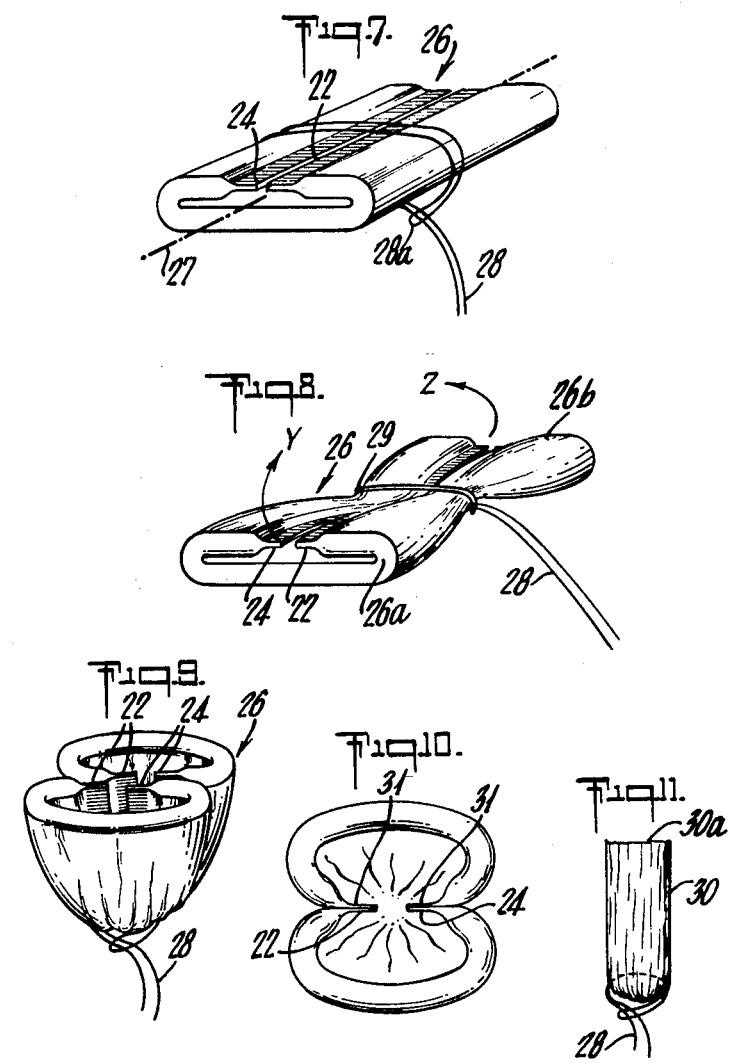

METHOD OF MAKING TAMPON WITH A NON-WOVEN WRAP

This is a division of application Ser. No. 99,771, filed Dec. 3, 1979, U.S. Pat. No. 4,294,253.

BACKGROUND OF THE INVENTION

The invention relates to a tampon with a withdrawal cord, especially for female hygiene, in which absorbent material is surrounded by a cover of material which is permeable to liquids and is compressed into an approximately cylindrical shape.

A tampon of this type, prior to its shaping, consisting of a covering layer capable of absorption, a layer of a hydrocolloid absorption agent and a layer for firmly holding the absorption agent, is known from German Laid-Open Application DOS No. 1,642,072. The first mentioned layer and the last mentioned layer are manufactured from a material which is permeable to liquids, for example nonwoven, paper or textile fabric. Optionally these layers can also be manufactured from a material which is not capable of absorption and they can be provided with openings of a greater or lesser size, for example a perforated polyethylene film. One of the longitudinal edges is folded over and the material is rolled up further so that a cylindrical blank is formed, the free edge of which is fixed by means of adhesive before the blank is compressed into the shape of the finished tampon. The withdrawal cord is fastened to the absorbent body by means of a seam or in another manner. A tampon in which a tube of material which absorbs liquid is folded together is known from German Laid-Open Application DOS No. 2,127,675.

U.S. Pat. Spec. No. 3,618,605 describes a cup-shaped tampon, of which the circular plates of material are superimposed, have a withdrawal cord drawn through their center and are then folded together, and compressed into the shape of a cup at the end opposite the exit of the withdrawal cord.

Furthermore, German Laid-Open Application DOS No. 2,324,264 discloses an absorbent body which contains a swelling material in its cover which is permeable to liquid, the cover being tubular and being closed either by drawing the ends together or along a longitudinal seam thereof. Part of the cover is folded inwards around one end thereof and around a part of the absorbent material present therein.

SUMMARY OF THE INVENTION

It is the object of the invention to so improve a tampon of the known type initially mentioned that this tampon can be manufactured simply and economically in mass production whilst exploiting all the advantages associated with a cup-shape.

According to the invention, this object is achieved when the cover with the absorbent material forms a flat cushion, the front and rear edges of which are folded onto the top side of the cushion with their ends facing one another, a withdrawal cord being fastened to the cushion approximately in the longitudinal direction of the latter, and the two pouch shaped side parts of the cushion which extend approximately perpendicular to the withdrawal cord are folded towards one another about the latter as the fold line and are compressed into the shape of the tampon.

Irrespective of how the flat cushion surrounding the absorbent material is initially formed, a large quantity of such tampons per unit time can be manufactured continuously in this manner since the folding of the front and rear edges onto the top side of the cushion and the fastening of the withdrawal cord as well as the folding of the side parts, which extend laterally to the withdrawal cord, towards one another and the subsequent final compression of the tampon can proceed in one continuous manufacturing process. At the same time, a closed cup-shape, having the known advantages, is obtained by the folding.

It is advantageous if, in the zone of the withdrawal cord which forms the fold line for the side parts, no absorbent material, or only a little absorbent material, is provided in the cushion. This substantially facilitates the folding of the two side parts of the cushion towards one another and provides the prerequisite for easily removing the finished tampon from the body cavity.

It can also be a particular advantage if the withdrawal cord loops around the cushion along the central longitudinal axis thereof. This ensures certain removal of the tampon from the body cavity and, in the case where no absorbent material, or only a little absorbent material, is present in the zone of the withdrawal cord, the latter so constricts the cover in the looping zone that the formation of the cup of the tampon is improved in this way.

A particularly good cohesion of the tampon which is cup-shaped as a result of the folds of the cushion, can be achieved when, after the pouch shaped side parts of the cushion have been folded towards one another, its front and rear edges which mutually face one another at half the width are joined to one another. This leads to improved properties in respect of a uniform expansion of the cup-shaped part of the tampon and to a reliable closure of the body cavity receiving the tampon.

From the point of view of manufacturing technology, it is particularly advantageous if the cover of the cushion consists of a longitudinal nonwoven ribbon, to which absorbent material is applied at successive intervals in the longitudinal direction thereof. In this case, the absorbent material can be applied on either side and at a distance from a longitudinal axis, preferably the central longitudinal axis of the nonwoven ribbon. Advantageously, the two longitudinal sides on the nonwoven ribbon are folded onto the top side of the longitudinal nonwoven ribbon section which lies between them, a tube being formed. Advantageously, the longitudinal sides which are folded onto the top side of the nonwoven ribbon are joined to one another. This provides a tube which forms a firm outward joint.

In a further advantageous embodiment, the layers of the tubular nonwoven ribbon, which are immediately superposed between the absorbent material inserts successively arranged at intervals in longitudinal direction of the tubular nonwoven ribbon, are joined to one another transversely to the longitudinal direction of the latter and cut through in such a way that the adjacent cut edges are closed by the formation of the respective front and rear edges of the cushion. In this way, the advantages of flow-line manufacture are exploited to the full extent for the mass production of such a tampon.

Preferably, the nonwoven ribbon itself consists of a nonwoven weldable material. This enables the sections of the tubular nonwoven ribbon, which run between the absorbent material inserts, to be joined to one another by welding in the transverse direction over such a width that, after the subsequent transverse cutting, the cut edges form, without further action, the front and rear edges of the cushion which have already been closed by the welding. Since the welded edges lie inside the cup, the body walls only come into contact with the welded cover material.

A further advantageous feature provides that, prior to applying absorbent materials to the nonwoven ribbon a continuous narrow film which is impermeable to moisture is applied extending in the longitudinal direction of the nonwoven ribbon. In this way, that part of the cushion cover which is surrounded by the withdrawal cord is reinforced and additionally sealed so that a breakthrough of liquid at the withdrawal end of the tampon is prevented.

The absorbent material within the cushion consists at least in part of a finely particulate polymerized hydrocolloid which is insoluble in water. This hydrocolloid possesses an exceptionally high capacity for absorbing and retaining liquid.

BRIEF DESCRIPTION OF THE DRAWINGS

The invention is illustrated, by way of example and diagrammatically, in the drawing in which:

FIG. 1 shows a nonwoven ribbon with a strip of film which is impermeable to moisture being applied thereon and with absorbent material inserts arranged at intervals successively and side by side, the nonwoven ribbon being in part folded inwards to form a tube;

FIG. 2 shows a plan view of a cushion which has been manufactured from the nonwoven ribbon in FIG. 1 and encloses the absorbent material inserts;

FIGS. 3 to 5 show various embodiments of the cushion, in section along line III—III in FIG. 2;

FIG. 6 shows a perspective view, partially cut open, of the cushion according to FIG. 2, with the front and rear edges folded up at right angles;

FIG. 7 shows a perspective view of the cushion according to FIG. 6, with the front and rear edges folded over onto the top side of the cushion and with a withdrawal cord surrounding the cushion in the longitudinal direction thereof;

FIG. 8 shows the cushion of FIG. 7 with a more tightly drawn loop of the withdrawal cord;

FIG. 9 shows the perspective view of the tampon blank with the side parts folded upward towards one another about the withdrawal cord as the fold line;

FIG. 10 shows a plan view of the opening, of the tampon blank of FIG. 9, which is cup-shaped and forms the introduction end of the tampon; and FIG. 11 shows a side view of the tampon blank according to FIGS. 9 and 10, after it has been compressed, in the direction transversely to the longitudinal axis of the blank, into the finished shape of the tampon.

DETAILED DESCRIPTION OF THE INVENTION

The sequence of FIGS. 1 to 11 corresponds to the manufacturing phases of the tampon according to the invention.

FIG. 1 shows a nonwoven ribbon 10 which is permeable to moisture, with a thin narrow film 14 being continuously placed on the longitudinal centre of the nonwoven ribbon, symmetrically to the central longitudinal axis 18 thereof. This film can consist of paper treated with plastic or wax, of plastic or of similar tear resistant materials which are impermeable to water. Preferably, the material of the film is heat sealable. Optionally, the use of this film can also be dispensed with.

Moreover, absorbent material inserts 16 are applied to the nonwoven ribbon and to the film 14, and these are arranged side-by-side at approximately equal lateral intervals from the central longitudinal axis 18 and successively at equal intervals in the longitudinal direction of the nonwoven ribbon. Each of the absorbent material inserts 16 covers a part of the film 14 and of the nonwoven ribbon which in each case extends to one side of the film. Alternatively to the illustrative embodiment shown in FIG. 1, it is possible, in place of an arrangement with pairs of adjacent absorbent material inserts in the transverse direction of the nonwoven ribbon only to provide a single absorbent material insert in each case which, accordingly, extends over the central longitudinal axis 18. In this case, however, it is advisable for the reasons described below to use a smaller amount of absorbent material in the zone of the central longitudinal axis 18. It is also possible to arrange the absorbent material insert or inserts along a longitudinal axis which is at a distance from and parallel to the central longitudinal axis 18, or to provide an asymmetrical distribution of the absorbent material inserts in the transverse direction of the nonwoven ribbon. In the latter case, for example, the inserts which are on the left in FIG. 1 can be narrower and the inserts which are on the right in FIG. 1 can be wider and the line which fixes the mutual distance of the inserts and aligns them along the longitudinal direction of the nonwoven ribbon can be offset with respect to the central longitudinal axis 18 of the nonwoven ribbon.

The longitudinal sides 10a, 10b of the nonwoven ribbon 10, which laterally project beyond the absorbent material inserts 16, are folded, by means of shaped shoulders which are not shown, onto the top side of the longitudinal nonwoven ribbon section which lies between them, a tube 10c being formed. As FIGS. 3 and 5 show, these longitudinal sides can merely overlap, or the lower of these sides can, as FIG. 4 shows, be folded over outwards before the two longitudinal sides are firmly jointed to one another by means of a weld seam 12 and thus extend in the longitudinal direction of the nonwoven ribbon shaped as a flat tube. As an alternative thereto, the longitudinal sides of the nonwoven ribbon can also be joined merely with an adhesive tape.

In FIG. 1, the absorbent material inserts are shown as structures of rectangular shape, which extend in the longitudinal direction and which consist at least in part of granular, fibrous or another finely particulate hydrocolloid which is insoluble in water and is polymerized, and which optionally can have a plate-like shape. However, it is also possible to apply the hydrocolloid in the form of sponges or crumbs of foam and in any other actual shape. In every case, however, it is advisable that preferably no absorbent material 16, or only small amounts thereof, are applied in the zone of the longitudinal central axis 18 of the nonwoven ribbon 10 and that none is applied in the zone of the transverse lines 20 under any circumstances since, as is described below, the nonwoven ribbon is folded about the longitudinal central axis 18 and is preferably welded, or alternatively sealed or adhesively bonded, and cut through along the transverse axis 20.

After the manufacture of the tubular nonwoven ribbon, the superposed layers of the nonwoven ribbon 10, which extend between the absorbent material inserts 16 successively arranged at intervals, are joined to one another along the transverse axis 20 between the absorbent material inserts, the film 14, if present, being included in this joint. This joining is preferably carried out by heat sealing or welding, but it can also be effected by adhesive bonding. It is essential here that the superposed layers of the nonwoven ribbon, as viewed in the longitudinal direction thereof, are joined to one another on such a surface area that sections of the flat tubular nonwoven ribbon, which each contain a pair of absorbent material inserts 16, can continuously be separated off through these mutually joined layers of the nonwoven ribbon along the transverse axis 20 in such a way that the adjacent cut edges of the preceding and succeeding sections of the tubular nonwoven ribbon form, respectively, the rear or front edge, in the direction of the arrow X, of the preceding or succeeding section of nonwoven ribbon and that these edges are closed as a result of the prior joining of the superposed layers of the nonwoven ribbon, even though they have been cut through. In this way, the sections of nonwoven ribbon form rectangular cushions 26 which are closed on all sides and which each contain a pair of absorbent material inserts 16.

FIG. 2 shows a cushion 26 of this type, which in plan view is rectangular, the longitudinal axis of this rectangle pointing in a direction transverse to the central longitudinal axis or the longitudinal seam 12 of the nonwoven ribbon or nonwoven cushion. Accordingly, the edge 22 which is the front edge in the longitudinal direction of the nonwoven ribbon 10, and likewise the rear edge 24 are each closed by approximately one half of the weld seam, previously made, between two successive sections of nonwoven ribbon.

FIG. 3 shows a cross-sectional shape of an embodiment of a cushion of this type, wherein, as already mentioned above, the longitudinal sides of the nonwoven ribbon 10 overlap and are joined by a weld seam 12, whilst the film 14 extends on the opposite side in the longitudinal center across a part of the absorbent material inserts 16. In FIG. 4, as mentioned, the outer edge of the inner longitudinal side is folded over outwards and the outer longitudinal side is likewise welded at 12 onto this part which is folded over outwards. The cushion here also contains a section of film 14. FIG. 5 differs from FIG. 3 merely in that the film 14 has here been omitted.

According to FIG. 6, the front edge 22 and the rear edge 24 which run transversely to the longitudinal seam 12 are both angled off upwards at right angles about the fold lines 25a, 25b which are parallel to the edges, and are subsequently folded around, according to FIG. 7, onto the top side of the cushion 26 in such a way that the ends of the two edges face one another at a small distance in the zone of this transverse central axis 27. The two free ends of a withdrawal cord 28 are then drawn through a loop 28a thereof and are tightened a little more according to FIG. 8 so that the cushion assumes the constricted shape. The withdrawal cord 28 extends in that vertical longitudinal section plane of the cushion 26 in which the longitudinal weld seam 12 or the central longitudinal axis 18 lies, that is to say in that zone which, according to the illustrative embodiment shown, is not filled with absorbent material. Therefore, this waisting 29 of the cushion in FIG. 8 can be accomplished without difficulty.

Subsequently, the pouch shaped side sections 26a, 26b of the cushion, which extend perpendicular to the looping plane of the withdrawal cord 28, are folded towards one another in the direction of the arrows Y, Z, as figure shows.

The length sections of the front edge 22 and the rear edge 24 of the cushion, which each extend to either side, now lie in contact with one another. In this case it is advantageous once more to join these edges, which are in contact with one another, in the plane designated as 31 in FIG. 10, and this in turn can preferably be effected by welding, but optionally also by sealing or adhesive bonding. Thereafter, the tampon blank according to FIGS. 9 and 1, which diverges into the shape of a cup towards the introduction end 30a of the finished tampon 30 in FIG. 11, is compressed in any desired manner, which is not shown in more detail, radially to a central longitudinal axis, running perpendicular to the plane of the drawing in FIG. 10, of the cup-shaped tampon blank to give the approximately cylindrical final shape of the tampon shown in FIG. 11. The fact that the edges 22, 24 come to lie in the inner zone of the cup-shaped blank or of the tampon ensures that only sections of the outer wall of the cup-shaped blank which are permeable for moisture or liquid to the full extent come into contact with the body wall since the compressed tampon in FIG. 11, when it absorbs liquid, assumes the shape illustrated in FIGS. 9 and 10, because the hydrocolloid forming the absorbent material swells up inside the cover. Optionally the hydrocolloid can be mixed here with other materials capable of absorption, for example with natural fibres, such as cotton fibres, cellulose fibres and the like. The tampon according to the invention is particularly suitable for use in conjunction with an applicator.

What is claimed is:

1. A method of making catamenial tampons comprising:
    depositing absorbent material in successive longitudinal intervals upon a longitudinally extending web of liquid permeable material having longitudinally extending side edges;
    folding the edges of the web over said absorbent material and sealing the edges together to form a sleeve containing said absorbent material;
    severing and transversely sealing said folded web at said longitudinal intervals to form flat cushions of absorbent material enveloped by said web, said transverse seals constituting front and rear edges of said flat cushions and said cushions each having a top face;
    folding each of said cushions into longitudinally successive sections consisting of a front section defined by said front edge and a first fold line, a central section defined by said first fold line and a second fold line and a rear section defined by said second fold line and said rear edge, said front and rear sections being folded onto the top face of said central section about said front and rear fold lines, respectively, with said front and rear edges facing one another;
    fastening a withdrawal cord around each of said folded cushions and dividing said cushion therewith into two lateral sections;
    folding the two lateral sections toward each other about said withdrawal cord with the folded front and rear sections facing each other; and compressing said folded cushions into a cylindrical tampon shape.

2. The method of claim 1 wherein the absorbent material is deposited on either side of and at a distance from a longitudinal axis of web of liquid pervious material.

3. The method of claim 1 wherein the web is weldable and said longitudinal edges of the web are heat sealed.

4. The method of claim 1 wherein the web is weldable and said front and rear edges are heat sealed.

5. The method of claim 1 wherein a reinforcing strip is applied to the liquid pervious web in the area underlying the withdrawal cord.

* * * * *